United States Patent
Do et al.

(10) Patent No.: US 11,826,341 B2
(45) Date of Patent: Nov. 28, 2023

(54) BAICALEIN ANALOGS FOR USE IN NEUROPROTECTION AND REGULATION OF IMMUNE REACTIVITY

(71) Applicants: THE HONG KONG POLYTECHNIC UNIVERSITY, Hong Kong (CN); The Schepens Eye Research Institute, Inc., Boston, MA (US)

(72) Inventors: Chi Wai Do, Hong Kong (CN); Chi ho To, Hong Kong (CN); Li Pan, Hong Kong (CN); Dongfeng Chen, Boston, MA (US); Kin-Sang Cho, Boston, MA (US)

(73) Assignees: THE HONG KONG POLYTECHNIC UNIVERSITY, Hong Kong (CN); The Schepens Eye Research Institute, Inc.

( * ) Notice: Subject to any disclaimer, the term of this patent is extended or adjusted under 35 U.S.C. 154(b) by 0 days.

(21) Appl. No.: 17/650,387

(22) Filed: Feb. 9, 2022

(65) Prior Publication Data
US 2022/0249432 A1    Aug. 11, 2022

Related U.S. Application Data (60) Provisional application No. 63/200,018, filed on Feb. 10, 2021.

(51) Int. Cl.
*A61K 31/352* (2006.01)
*A61P 27/02* (2006.01)

(52) U.S. Cl.
CPC ............ *A61K 31/352* (2013.01); *A61P 27/02* (2018.01)

(58) Field of Classification Search
CPC .................................................. A61K 31/352
See application file for complete search history.

(56) References Cited

PUBLICATIONS

Chao; Journal of Ocular Pharmacology and Therapeutics 2013, 29, 539-549. https://doi.org/10.1089/jop.2012.0179 (Year: 2013).*
Li; International Journal of Biological Macromolecules 2020, 156, 749-761. https://doi.org/10.1016/j.ijbiomac.2020.04.115 (Year: 2020).*
Li; Invest. Ophthalmol. Vis. Sci. 2017, 58, 4466. (Year: 2017).*
Liu; Journal of Ocular Pharmacology and Therapeutics 2010, 26, 421-429. https://doi.org/10.1089/jop.2010.0063 (Year: 2010).*
Maher; Experimental Eye Research 2008, 86, 366-374. https://doi.org/10.1016/j.exer.2007.11.009 (Year: 2008).*
Majumdar; Journal of Pharmacy and Pharmacology 2010, 62, 951-965. https://doi.org/10.1211/jpp.62.08.0001 (Year: 2010).*
Pan; Oxidative Medicine and Cellular Longevity 2021, 8377362. https://doi.org/10.1155/2021/8377362 (Year: 2021).*
Pan; Front. Immunol. 2022, 13, 837497. https://doi.org/10.3389/fimmu.2022.837497 (Year: 2022).*
Sowndhararajan; Biomedicine & Pharmacotherapy 2017, 95, 1021-1032. http://dx.doi.org/10.1016/j.biopha.2017.08.135 (Year: 2017).*
Xiao; Journal of Ocular Pharmacology and Therapeutics 2014, 30, 605-614. https://doi.org/10.1089/jop.2014.0074 (Year: 2014).*
Zhang; Current Eye Research 2009, 34, 257-263. https://doi.org/10.1080/02713680902725962 (Year: 2009).*
Clark; Exp. Eye Res. 2013, 116, 433. http://dx.doi.org/10.1016/j.exer.2013.08.002 (Year: 2013).*

* cited by examiner

*Primary Examiner* — Daniel R Carcanague
(74) *Attorney, Agent, or Firm* — S&F/WEHRW (57) ABSTRACT

A method of treating an ocular nerve injury in a subject in need thereof, the method comprising administering a therapeutically effective amount of baicalein or an analog thereof.

6 Claims, 9 Drawing Sheets
(2 of 9 Drawing Sheet(s) Filed in Color)

BAICALEIN ANALOGS FOR USE IN NEUROPROTECTION AND REGULATION OF IMMUNE REACTIVITY

CROSS-REFERENCE TO RELATED APPLICATIONS

This application claims priority from U.S. Provisional Patent Application No. 63/200,018, filed on Feb. 10, 2021, which is incorporated herein by reference in its entirety.

BACKGROUND

Glaucoma is a severe eye disease often resulting in permanent loss of vision. It is an optic neuropathy with unclear pathogenesis manifested by a progressive loss of retinal ganglion cells (RGCs). Elevated intraocular pressure (IOP) is widely recognized as an important risk factor for glaucoma. Lowering IOP continues to be the mainstay of treatment. Pharmacological treatment and surgical interventions targeted at IOP reduction remains the only clinical intervention documented to be effective in delaying glaucomatous progression. However, undesirable side effects are frequently reported in these anti-glaucoma medications. On the other hand, retinal ischemia and reperfusion injury is a common pathological condition found in many retinal diseases, causing irreversible visual impairment and blindness. Currently, the therapeutic options for neuronal cell death are very limited. Neuroprotection has been suggested to have a therapeutic potential for delaying the progression of various retinal diseases including glaucoma, but has not yet been successfully developed as a clinical treatment.

Baicalein (5,6,7-trihydroxyflavone; $C_{15}H_{10}O_5$) is a major flavonoid isolated from the roots of *Scutellaria baocalensis* Georgi (SB), which is a medicinal herb and has been widely used in many Asian countries. The literature has shown that baicalein and analogs thereof have a broad spectrum of bioactivity.

There thus exists a need for improved methods for neuroprotection that address at least some of the needs described above.

SUMMARY

In a first aspect, provided herein is a method of a method of treating an ocular nerve injury in a subject in need thereof, the method comprising administering a therapeutically effective amount of a compound to the subject, wherein the compound has Formula I:

I or a pharmaceutically acceptable salt thereof, wherein
m is a whole number selected from 0-2;
$R^1$ and $R^3$ are each independently selected from the group consisting of —OR, —O(C=O)R, —O(C=O)OR, —O(C=O)NR$_2$, and —O(P=O)(OH)$_2$;
$R^2$ and $R^4$ are each independently selected from the group consisting of hydrogen; —OR, —O(C=O)R, —O(C=O)OR, —O(C=O)NR$_2$, and —O(P=O)(OH)$_2$;
$R^5$ for each instance is independently selected from the group consisting of halide, nitro, cyanide, —OR, —O(C=O)R, —O(C=O)OR, —O(C=O)NR$_2$, —O(P=O)(OH)$_2$, —NR$_2$, —N(R)(C=O)R, —N(R)(C=O)OR, and —N(R)(C=O)NR$_2$; and
R for each instance is independently selected from the group consisting of hydrogen, alkyl, alkenyl, alkynyl, cycloalkyl, aryl, heteroaryl, aralkyl, and a glucuronic acid.

In certain embodiments, at least one of $R^2$ and $R^4$ is hydrogen.

In certain embodiments, $R^1$ and $R^3$ are each independently selected from the group consisting of hydrogen, —OH, —OMe, and —O(P=O)(OH).

In certain embodiments, $R^1$-$R^3$ are each —OH; and $R^4$ is hydrogen; $R^1$ and $R^3$ are each —OH; $R^2$ is hydrogen; and $R^4$ is —OMe; $R^1$ and $R^3$ are —OH; and $R^2$ and $R^4$ are hydrogen; or $R^1$ and $R^2$ are each —OH; R is —O-glucuronic acid.

In certain embodiments, the compound is selected from the group consisting of:

,

,

, and

,

, or a pharmaceutically acceptable salt thereof.

In certain embodiments, the ocular nerve injury is the result of an ischemia injury, an ischemia-reperfusion injury, trauma, blast, glaucoma, optic neuritis or an optic neuropathy.

In certain embodiments, the ocular nerve injury comprises an injured retinal ganglion cell.

In certain embodiments, administration of the compound at least partially inhibits PI3K and NFkB pathway activation in the subject In certain embodiments, administration of the compound at least partially inhibits expression of IL-1β and TNFα in the subject.

In certain embodiments, the subject is a human.

In certain embodiments, the compound is administered intravitreally, intraperitoneally, suprachoroidally, subconjunctivally, retrobulbarly, intracamerally, or subretinally.

In certain embodiments, the compound is:

or a pharmaceutically salt thereof; the compound is administered intravitreally; and the nerve injury comprises a retinal ganglion cell injury.

In a second aspect, provided herein is a method of treating an ocular neuron, the method comprising contacting the ocular neuron with a compound, wherein the compound has Formula I:

or a pharmaceutically acceptable salt thereof, wherein m is a whole number selected from 0-2;
$R^1$ and $R^3$ are each independently selected from the group consisting of —OR, —O(C=O)R, —O(C=O)OR, —O(C=O)NR$_2$, and —O(P=O)(OH)$_2$;
$R^2$ and $R^4$ are each independently selected from the group consisting of hydrogen; —OR, —O(C=O)R, —O(C=O)OR, —O(C=O)NR$_2$, and —O(P=O)(OH)$_2$;
$R^5$ for each instance is independently selected from the group consisting of halide, nitro, cyanide, —OR, —O(C=O)R, —O(C=O)OR, —O(C=O)NR$_2$, —O(P=O)(OH)$_2$, —NR$_2$, —N(R)(C=O)R, —N(R)(C=O)OR, and —N(R)(C=O)NR$_2$; and
R for each instance is independently selected from the group consisting of hydrogen, alkyl, alkenyl, alkynyl, cycloalkyl, aryl, heteroaryl, aralkyl, and a glucuronic acid.

In certain embodiments, at least one of $R^2$ and $R^4$ is hydrogen.

In certain embodiments, $R^1$ and $R^3$ are each independently selected from the group consisting of hydrogen, —OH, —OMe, and —O(P=O)(OH).

In certain embodiments, $R^1$-$R^3$ are each —OH; and $R^4$ is hydrogen; $R^1$ and $R^3$ are each —OH; $R^2$ is hydrogen; and $R^4$ is —OMe; $R^1$ and $R^3$ are —OH; and $R^2$ and $R^4$ are hydrogen; or $R^1$ and $R^2$ are each —OH; $R^3$ is —O-glucuronic acid.

In certain embodiments, the compound is selected from the group consisting of:

, and

,

, or a pharmaceutically acceptable salt thereof.

In certain embodiments, the injured neuron is an injured retinal ganglion cell.

In certain embodiments, the ocular neuron is contacted with the compound at a concentration between 10-200 μM.

In certain embodiments, the compound is:

or a pharmaceutically salt thereof; the ocular neuron is an injured retinal ganglion cell; and the injured retinal ganglion cell is contacted with the compound at a concentration between 10-100 µM.

The neuroprotective effects of baicalein and analogs thereof were studied on retinal functional responses, morphological and histological retinal changes in mice with retinal ischemia/reperfusion injury. The results showed that intravitreal injection of baicalein improved visual acuity and contrast sensitivity of mice with retinal ischemia damages resulted from acute ocular hypertension. Electroretinography (ERG) results illustrated that responses from photoreceptors, bipolar cells and retinal ganglion cells (RGCs) were functionally rescued by baicalein. Histological findings also showed that baicalein significantly protected the RGCs loss against ocular hypertension. In addition, we have demonstrated that baicalein suppresses the microglia activation and expression of pro-inflammatory factors such as IFNg, IL-6 on CD4+ T cells in the eye drainage lymph node, superior cervical lymph node, following ischemia/reperfusion damage. Moreover, baicalein is shown to protect RGCs from death in culture. Taken together, our data suggest that baicalein may represent a naturally occurring neuroprotective molecule by protecting neuronal degeneration and suppressing inflammatory microglia and CD4+ T cells activities.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects and features of the present disclosure will become apparent from the following description of the disclosure, when taken in conjunction with the accompanying drawings.

DETAILED DESCRIPTION

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, +7%, ±5%, ±3%, ±1%, or +0% variation from the nominal value unless otherwise indicated or inferred.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein, the term "subject" refers to any animal (e.g., a mammal), including, but not limited to, humans, non-human primates, canines, felines, and rodents.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like The term "nitro" is art-recognized and refers to $NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2$—. "Halide" designates the corresponding anion of the halogens, and "pseudohalide" has the definition set forth on 560 of "Advanced Inorganic Chemistry" by Cotton and Wilkinson.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. The present invention contemplates all such compounds, including E- and Z-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The present disclosure provides a method for of treating an ocular nerve injury in a subject in need thereof, the method comprising administering a therapeutically effective amount of a compound to the subject, wherein the compound has Formula I.

or a pharmaceutically acceptable salt thereof, wherein m is a whole number selected from 0-2;

$R^1$ and $R^3$ are each independently selected from the group consisting of —OR, —O(C=O)R, —O(C=O)OR, —O(C=O)NR$_2$, and —O(P=O)(OH)$_2$;

$R^2$ and $R^4$ are each independently selected from the group consisting of hydrogen; —OR, —O(C=O)R, —O(C=O)OR, —O(C=O)NR$_2$, and —O(P=O)(OH)$_2$;

$R^5$ for each instance is independently selected from the group consisting of halide, nitro, cyanide, —OR, —O(C=O)R, —O(C=O)OR, —O(C=O)NR$_2$, —O(P=O)(OH)$_2$, —NR$_2$, —N(R)(C=O)R, —N(R)(C=O)OR, and —N(R)(C=O)NR$_2$; and R for each instance is independently selected from the group consisting of hydrogen, alkyl, alkenyl, alkynyl, cycloalkyl, aryl, heteroaryl, aralkyl, and a glucuronic acid.

m can be 0, 1, or 2. In certain embodiments, m is 0.

In certain embodiments, $R^1$ and $R^3$ are each independently —OH, —O(P=O)(OH)$_2$, or —O-glucuronic acid. In instances in which $R^1$ and/or $R^3$ is —O-glucuronic acid, the chemical structure of —O-glucuronic acid can be represented by the moiety:

In certain embodiments, $R^2$ and $R^4$ are each independently hydrogen, —OH, —O-alkyl, or —O(P═O)(OH)$_2$. In certain embodiments, $R^2$ and $R^4$ are each —OH.

In certain embodiments, $R^5$ for each instance is independently selected from the group consisting of halide, nitro, cyanide, —OH, —O(P═O)(OH)$_2$, and —NR$_2$.

In certain embodiments, R for each instance is independently selected from the group consisting of hydrogen, alkyl, alkenyl, alkynyl, cycloalkyl, aryl, heteroaryl, aralkyl, and a glucuronic acid. In certain embodiments, each R is independently selected from the group consisting of hydrogen and $C_1$-$C_6$ alkyl.

In certain embodiments, the compound is selected from the group consisting of:

or a pharmaceutically acceptable salt thereof.

The ocular nerve injury can be acute or chronic. An ocular nerve injury can comprise the complete severing or partial severing of a neuron, or crushing or compression injury to a neuron. In certain embodiments, the ocular nerve injury directly impairs the normal functioning of neuron(s). In certain embodiments, the ocular nerve injury indirectly impairs the normal functioning of the neuron(s). The ocular nerve injury can result from an acute or traumatic event, chronic event, pressure build-up, or chronic neurodegeneration. Injuries to a subject can result in injury to a neuron. Common causes of nervous system injury include, but are not limited to, disease and/or infection, ischemia, anoxia, hypoglycemia, contusion, laceration, damage by exogenous chemical agents, and combinations thereof.

The ocular nerve injury can be the result of an ischemia injury, an ischemia-reperfusion injury, and glaucoma.

In certain embodiments, the subject that suffers from an ocular nerve injury resulting from a trauma. The ocular nerve injury may comprise injury to the optic nerve. In certain embodiments, the optic nerve comprises a retinal ganglion cell.

In certain embodiments, the subject that suffers from an injury caused by or associated with neuropathies, such as diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy; and/or peripheral nerve damage associated with spinal cord injury.

Administration of a therapeutically effective amount of a compound described herein to the subject can result in at least the partial inhibition of PI3K and NFkB pathway activation in the subject.

Administration of a therapeutically effective amount of a compound described herein to the subject can result in at least the partial inhibition of expression of IL-1β and TNFα in the subject.

In certain embodiments, the compound described herein is administered to the subject by any one or a combination of methods selected from the group consisting of intravitreally, intraperitoneally, suprachoroidally, subconjunctivally, retrobulbarly, intracamerally, and subretinally. In certain embodiments, the compounds described herein are administered to the subject intravitreally.

The mode of administration for the compounds described herein may be any suitable route that delivers the agent to the subject, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, suspension, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

In certain embodiments, the compound is administered to the eye. In instances in which the compound is administered to the eye, the route of administration can be selected from intravitreal injection, topical, intracameral injection, subconjunctival injection, sub-tenon injection, retro bulbar injection, sub-retinal injection, and peri-ocular or laterobulbar injection.

In certain embodiments, the compounds described herein are administered to the subject in the form of smoke, steam, or nebulized powder or gas comprising the compound described herein. In other embodiments, the compound described herein is administered by application of a medicated pillow, a medicated eyepad, or other aromatic sachet comprising the compound described herein.

Specific routes of administration and the dosage regimen will be determined by skilled clinicians, based on factors such as the exact nature of the condition being treated, the severity of the condition, and the age and general physical condition of the patient.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens. In certain embodiments, the compounds described herein are administered to the subject on a once daily, once weekly, twice weekly, thrice weekly, once monthly, or twice monthly basis.

While the dosage will vary depending on the subject's age, body weight, symptom to be treated, desired therapeutic effect, administration route, term of treatment and the like, satisfactory effects can be obtained with the dosage of 0.001-200 μg/eye administered locally or 0.001-500 mg/kg administered systemically in 1 to 5 divided doses a day or as a sustained form.

In certain embodiments, the method for treating an nerve injury in a subject in need thereof comprises co-administering a therapeutically effective amount of a compound described herein and a therapeutically effective amount of second therapeutic agent to the subject.

The second therapeutic agent can be any therapeutic agent known in the art to be useful in the treatment of glaucoma, an antibiotic, an anti-inflammatory agent, an anti-allergic agent, an artificial tear fluid, and the like. Exemplary second therapeutic agents include, but are not limited to, acetazolamide, diclofenamide, cartolol, timolol, metipranolol, betaxolol, pindolol, levobonolol, brimonidine, clonidine, pilocarpine, carbachol, dipivephrine, apraclosolidine, dorzolamide, bimatoprost, grass simple, latanoprost, chlortetracycline, ciprofloxacin, ofloxacin, fusidic acid, gentamicin, kanamycin, levofloxacin, lomefloxacin, oxytetracycline, natamycin, azidamphenicol, chloram obramycin, erythromycin, polymyxin-B, atsaclovir, trifluridine, betamethasone, dexamethasone, fluorometholone, hydrocortisone, prednisolone, rimexolone, cromoglycate, azelastine, lodoxamide, emedastine, nedocromil, levocabastine, hypotellomellus, carotomellomellum, povidone, hyetellose, polyvinyl alcohol, dexpanthenol, tetrizoline, troxerutin, tramazoline, naphazoline, xylometazoline, phenylephrine, antazoline, and the like.

The compound described herein can be administered according to therapeutic protocols well known in the art. It will be apparent to those skilled in the art that the administration of the compound described herein and the second therapeutic agent can be varied depending on the disease being treated and the known effects of the second therapeutic agent on that disease. Also, in accordance with the knowledge of the skilled clinician, the therapeutic protocols (e.g., dosage amounts and times of administration) can be varied in view of the observed effects of the administered therapeutic agents (i.e., second therapeutic agent) on the subject, and in view of the observed responses of the disease to the administered compound described herein.

Also, in general, the compound described herein and the second therapeutic agent do not have to be administered in the same pharmaceutical composition, and may, because of different physical and chemical characteristics, have to be administered by different routes. For example, the compound described herein may be administered intravenously to generate and maintain good blood levels, while the second therapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of second therapeutic agent will depend upon the diagnosis of the attending physicians and their judgment of the condition of the patient and the appropriate treatment protocol.

The compound described herein and the second therapeutic agent may be administered concurrently (e.g., simultaneously, essentially simultaneously or within the same treatment protocol) or sequentially, depending upon the nature of the disease, the condition of the patient, and the actual choice of second therapeutic agent to be administered in conjunction (i.e., within a single treatment protocol) with the compound described herein.

If compound described herein and the second therapeutic agent are not administered simultaneously or essentially simultaneously, then the optimum order of administration of the compound described herein and the second therapeutic agent, may be different for different diseases. Thus, in certain situations the compound described herein may be administered first followed by the administration of the second therapeutic agent; and in other situations the second therapeutic agent may be administered first followed by the administration of the compound described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the second therapeutic agent may be administered first and then the treatment continued with the administration of the compound described herein followed, where determined advantageous, by the administration of the second therapeutic agent, and so on until the treatment protocol is complete.

Thus, in accordance with experience and knowledge, the practicing physician can modify each protocol for the administration of a component (compound described herein and second therapeutic agent) of the treatment according to the individual patient's needs, as the treatment proceeds.

The present disclosure also provides a method of promoting growth, regrowth, and/or regeneration of a neuron, the method comprising contacting the neuron with a therapeutically effective amount of a compound described herein. Contacting the neuron can occur in vivo, in vitro or ex vivo. Neuron cells can be isolated from a subject and grown in vitro, using techniques well known in the art. The neuron may be a healthy neuron or an injured neuron. In certain embodiments, the neuron cell is a retinal ganglion cell. In certain embodiments ocular neuron is an injured ocular neuron.

The neuron cell may be isolated from a subject that suffers from an injury caused by or associated with peripheral neuropathies, such as diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy; and/or peripheral nerve damage associated with spinal cord injury.

The step of contacting the compound and the neuron cell can comprise contacting the neuron cell and the compound at a concentration between about 10 µM to about 200 µM, about 10 µM to about 150 µM, about 10 µM to about 100 µM, about 10 µM to about 50 µM, about 50 µM to about 100 µM, about 50 µM to about 200 µM, about 100 µM to about 200 µM, about 10 µM, or about 100 µM of the compound.

Treatment of the neuron cell may result in one or more of the growth or regeneration of the injured neuron.

EXAMPLES

Figure 1:
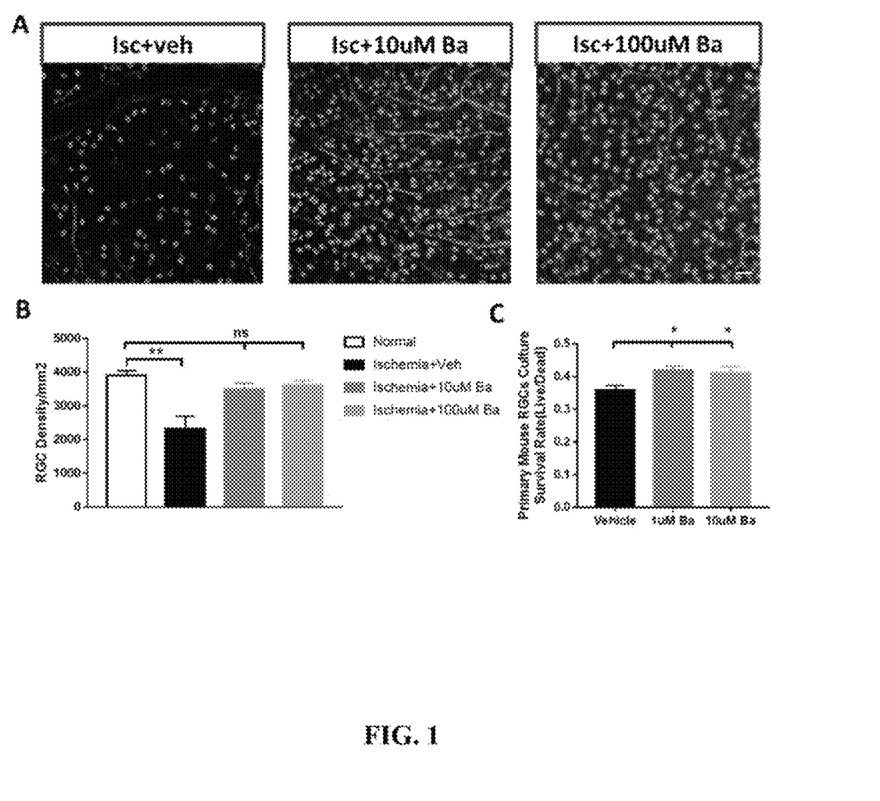
FIG. 1 depicts data demonstrating that baicalein improves RGC survival after ischemia/reperfusion damage in vivo and in vitro. (A) representative photomicrographs showing Brn-3a staining a whole-mounted retina from four weeks after ischemia injury in vehicle, 10 µM or 100 µM baicalein group; (B) bar graph quantifying the number of survived RGCs in 4 weeks post-injury retina from vehicle, 10 µM or 100 µM baicalein group; (C) bar graph the number of live primary RGC survival rate in vehicle, 1 µM baicalein group. Bar=20 µm. *P<0.05; **P<0.01 value was statistically analyzed by one-way ANOVA.

Example 1—Baicalein improves RGCs survival in vitro culture or after ischemia/reperfusion damages. To study the effect of baicalein on retinal neurons, we carried out in vitro RGC cultures and in vivo studies of RGCs survival in experimental models of retinal ischemia/reperfusion injury. RGC density dropped from 3,901+/−145 cells/mm$^2$ to 2,314+/−383 cells/mm$^2$ at 4 weeks following ischemia/reperfusion injury. Intravitreal injection of 10 µM and 100 µM baicalein day 1 after injury rescued RGCs from ischemia/reperfusion injury-induced damage and resulted in a significant increase of RGC density to 3,480+/−197 cells/mm$^2$ and 3,604+/−137 cells/mm$^2$, respectively, as compared to control/saline injected mice (FIGS. 1A and 1B). Moreover, purified mouse RGCs were cultured with vehicle, 1 µM or 10 µM Baicalein for 48 hours. RGCs in the vehicle group exhibited significantly lower survival rate (35.8+/−1.3%) compared to cultures treated with 1 µM (42.0+/−1.2%) and 10 µM (41.1+/−1.9%) baicalein (FIG. 1C). Both in vitro and in vivo studies demonstrated a protective effect of baicalein on RGC survival.

Figure 2:
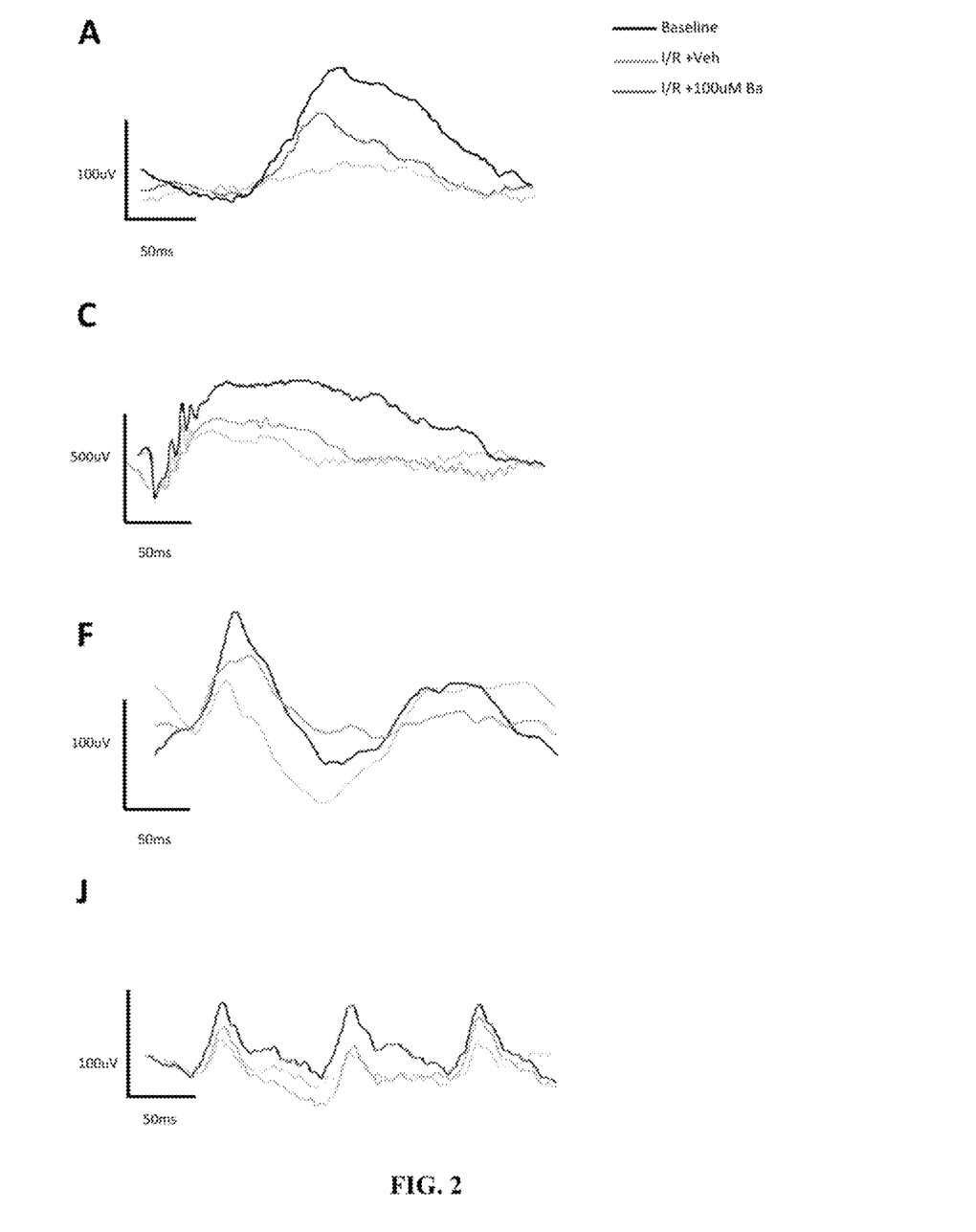
FIG. 2 depicts data demonstrating intravitreal administration of baicalein rescues visual functions in ischemia/reperfusion mice. (A) Representative waveform of pSTR, (C) Scotopic a and b wave, (F) M-cone and (J) 10 Hz flicker. Black curve: 100 µM baicalein; Dark Gray curve: 10 µM baicalein; and Gray curve; vehicle. (B)Graphs showing the amplitude of pSTR response, (D) Scotopic a and (E) b wave, (H) M-cone, and (I) 10 Hz flicker of ERG in mice received ischemia reperfusion and intravitreal injections of vehicle, 10 µM or 100 µM baicalein. (K) Graphs showing contrast sensitivity (CS) and (L) visual acuity (VA) of optomotor response (OMR) in mice received ischemia/reperfusion and intravitreal injections of vehicle, 10 µM or 100 µM baicalein. Error bar=SEM. *P<0.05; **P<0.01.

Visual functions were rescued after baicalein given post ischemia/reperfusion injury. The results of electroretinogram (ERG) and optomotor response (OMR) measurements were used to determine the changes of visual functions after ischemia/reperfusion damages. For ERG measurement, positive scotopic threshold response (pSTR), scotopic a- and b-wave, M-cone and 10 Hz flicker amplitudes were obtained from the three experimental groups (i.e. vehicle, 10 µM and 100 µM baicalein) at baseline, 1 wk, 2 wks and 4 wks post-ischemia/reperfusion injury (FIGS. 2A, 2B, 2C, 2D, 2E, 2F, 2G, 2H, 2I and 2J). The amplitudes of pSTR showed a reduction in the vehicle-treated group while a significant improvement was observed at 4-week in baicalein-treated group (100 µM) at both intensities. The improvement was also found at higher light intensity 1 week after ischemia/reperfusion injury (FIGS. 2A and 2B). Scotopic ERG including a wave and b wave among three groups at baseline, 1 wk, 2 wks and 4 wks after ischemia/reperfusion injury were monitored, and the protective effects of baicalein on bipolar cells were also identified (FIGS. 2C, 2D and 2E). At the same time, the electrical signals from M-cone and 10 Hz-flicker stimulus were also captured (FIGS. 2F, 2G, 2H, 2I and 2J). Compared to the decreased amplitudes of M-cone and 10-Hz Flicker, 100 µM baicalein given group presented improved rod and cone responses after the injury of ischemia/reperfusion.

For OMR measurement, all experimental groups showed a significant reduction of contrast sensitivity and visual acuity after ischemia damages (FIGS. 2K and 2L). Weekly administration of intravitreally-injected baicalein (100 µM) improved the contrast sensitivity and visual acuity 4 weeks after ischemia (FIGS. 2K and 2L). Even at 10 µM, baicalein demonstrated an improvement in visual acuity after ischemia injury (FIG. 2L). The results showed that 100 µM baicalein-treated group prevented the loss of a and b waves at 4 weeks compared to the vehicle-treated group (FIG. 2C).

Figure 3:
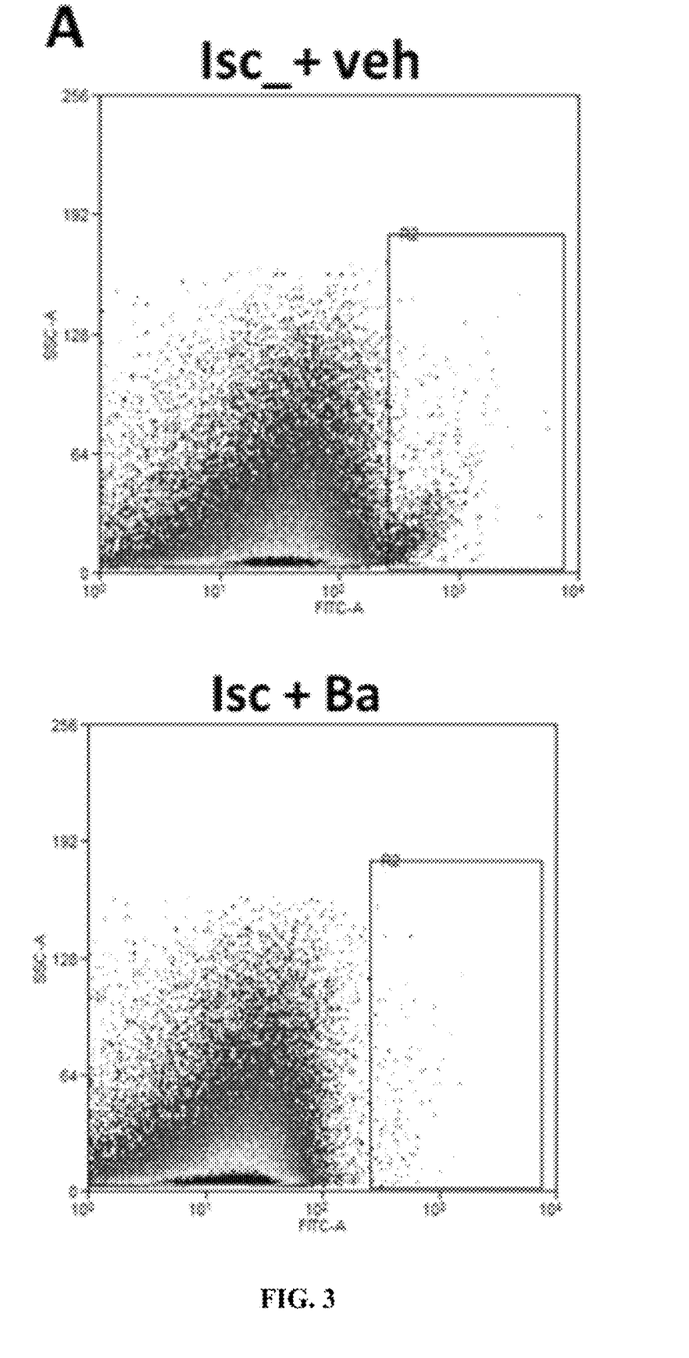
FIG. 3 Baicalein administration reduces the expression of pro-inflammatory factors from CD4+ T cells in the eye draining (superior cervical) lymph nodes after ischemia/reperfusion damage. (A) 1 wk representative flow images and (B) quantification of the CD4+ cell percentage in the retina at 1 wk and 4 wks timepoint. Flow cytometry quantification of frequencies of subsets of CD4+ T cells in the draining LNs of the eye taken from mice at 1 wk (C) and 4 wks (D) after acute ischemic injury in vehicle or 100 µM baicalein given group. Shown were percentages of CD4+ T cells that expressed IFN-γ, IL-17, IL-4, IL-10 or TGF-β among fresh-isolated total LN lymphocytes. Error bar=SEM. *P<0.05; **P<0.01

Baicalein administration reduces the infiltrated T cells in the retina and the activation of T cell subtypes in the superior cervical lymph nodes after ischemia/reperfusion damages. Eyes are widely known as an immune privileged site. However, ischemia and blood reperfusion in the retina will bring immune cells into the ischemia region and cause the immunological activation[1]. Priming of T cell responses usually occurs first in the secondary lymphoid tissues, such as lymph nodes (LNs)[15]. To assess whether baicalein suppresses the activation of inflammatory responses and T cell activations after ischemia/reperfusion injury in the retina and eye draining LNs, CD4+ T cells in the retina and superior cervical LNs were analyzed with flow cytometry. Surprisingly, baicalein given after ischemia/reperfusion injury not only decrease the number of infiltrated T cells in the retina, but also regulate functional T cell subsets in the LNs (FIGS. 3A, 3B, 3C and 3D). Th1, Th2, Th17, and Treg cells, again were divided based on the expression profile of hallmark cytokines: IFN-γ (TH1), IL-4 (TH2), IL-10 (TH2), IL-17 (TH17), and TGF-β (Treg)[16]. Superior cervical LNs were dissected from mice with retinal ischemia at 1- and 4-week post-injury receiving either vehicle or 100 µM baicalein. The results showed that IFNγ (TH1) was significantly inhibited at 1 and 4 weeks after ischemic injury in the baicalein-treated group (FIGS. 3C and 3D). The expressions of IL-10 (TH2) in the baicalein-treated group were lower than that of vehicle-treated at 4-week post-injury. IL-4 (TH2) level was found to be lower than vehicle group at 4-week time point. The results suggested that baicalein suppresses overall CD4+ cells penetration in the retina and activation in superior cervical LN after ischemia/reperfusion damage in the eyes.

Figure 4:
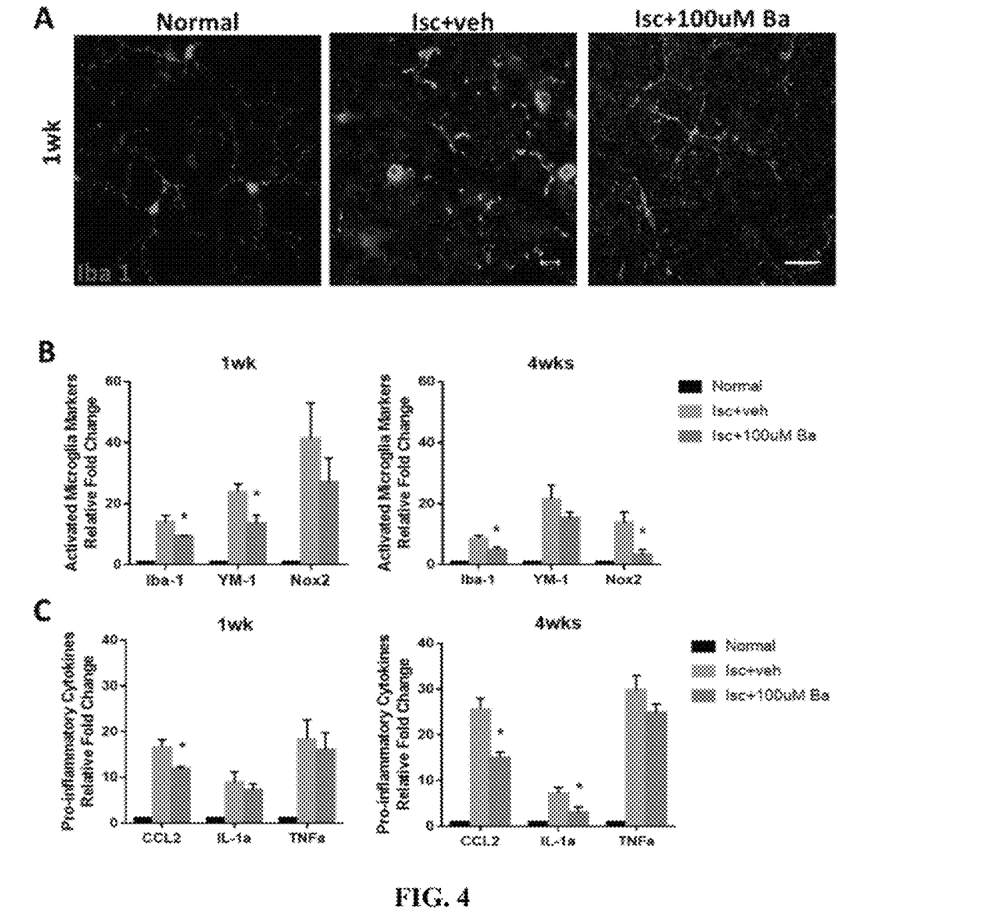
FIG. 4 Activated microglial cells in ischemia/reperfusion mice model were suppressed by baicalein administration. (A) Representative images of microglial cells immunolabeled with Iba-1 in normal mice and mice 1 wk post ischemia/reperfusion retina from vehicle or 100 µM baicalein given group. Scale bar=20 µm. Quantifications of qPCR assay showing the relative expression of (B) activated microglia markers and (C) pro-inflammatory cytokines in normal mice, and mice at 1 wk and 4 wks post ischemia/reperfusion retina from vehicle or 100 µM Ba given group. Error bar-SEM. *P<0.05.

Retinal microglia activation and pro-inflammatory factors expression were significantly suppressed by baicalein after ischemia/reperfusion injury. Microglial cells, the resident immune cell in retina, are responsible for the immune surveillance in the retina[17]. After ischemia/reperfusion induced damages to the retina, microglial cells activation was noticed at the early stage (FIG. 4A). Increased microglial cell density, enlarged cell body size and shorten dendrites were quantified in the retina post-ischemia/reperfusion injury by comparing with the morphology of microglia in normal retina. To verify the morphology changes showed in retinal microglial cells, mRNA levels of activated microglia markers were quantified by using qPCR. After 1- and 4-week post ischemia/reperfusion injury, 100 µM baicalein given retina presented relatively low mRNA levels of activated microglia markers such as Iba-1, YM-1 and Nox2 (FIG. 4B). Additionally, the pro-inflammatory cytokines including CCL2, IL-1α were down-regulated after baicalein given, compared with vehicle given group (FIG. 4C). Thus, the regulation of microglia activation and the expression of pro-inflammatory factors were involved in one of pathway which baicalein may played in the neuroprotective effects after ischemia/reperfusion injury.

Figure 5:
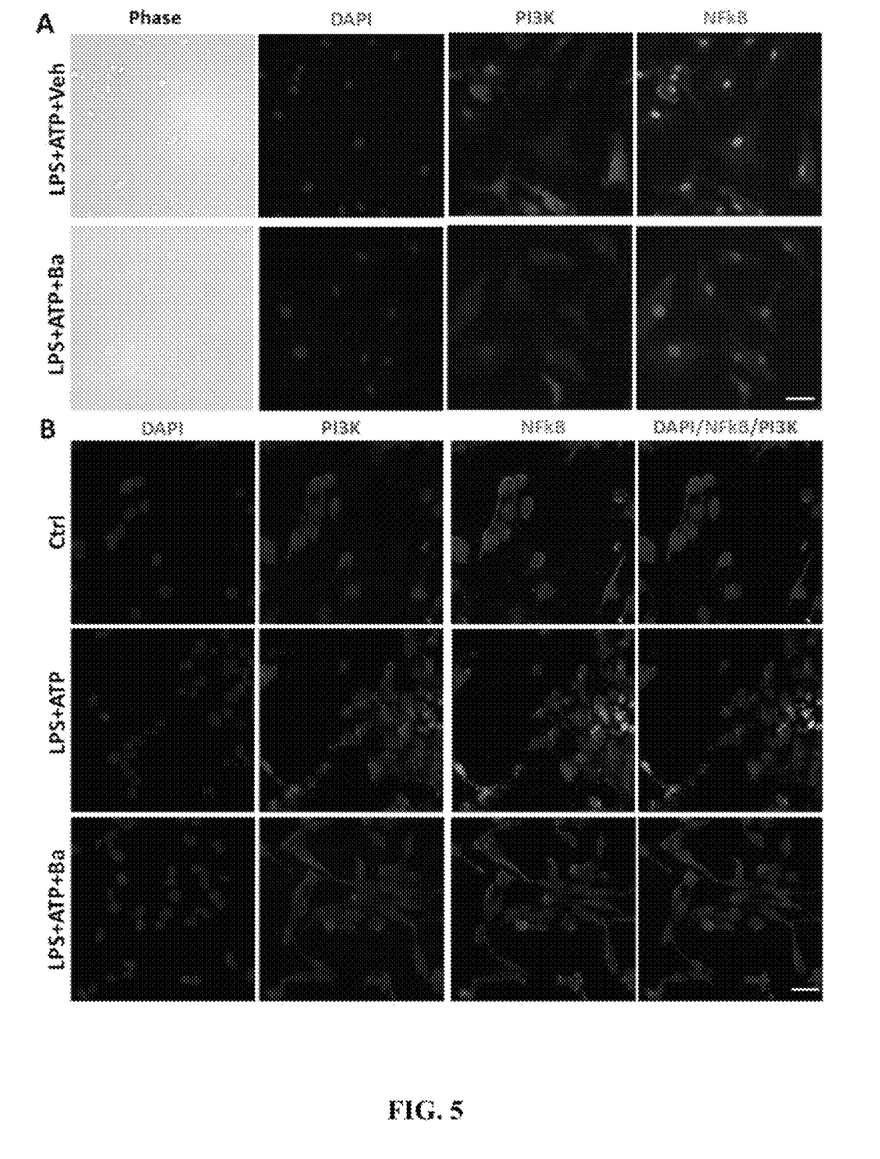
FIG. 5 Baicalein suppresses PI3K and NFkB pathway in both primary mouse brain microglia and human microglia HMC3 cell line in vitro. (A) Representative bright field images of primary mouse brain microglia and images immunostained with DAPI (blue), p85 PI3K (red) and p65 NFkB (green) antibody in LPS and ATP plus vehicle or 10 µM baicalein delivered group respectively. Scale bar=40 µm (B) Representative human microglia images immunostained with DAPI (blue), p85 PI3K (red) and p65 NFkB (green) antibody in LPS and ATP plus vehicle or 10 µM baicalein delivered group respectively. Error bar=SEM. *P<0.05; **P<0.01. Scale bar=100 µm.

PI3K and NFkB pathway were effectively suppressed by baicalein delivery in both primary mouse microglia and human microglial cell line HMC-3. To further understand if the effects of suppressing microglia activation and cytokines release are related with NFkB and PI3K pathway, we examine the performance of baicalein in primary mouse microglia and human microglial cell line HMC-3. As expected, compared to the upregulation of PI3K and NFkB in the LPS and ATP challenged mouse and human microglial cells, additional baicalein delivery can effectively reduce the PI3K and NFkB pathway activation in both mouse and human microglial cells (FIGS. 5A and 5B). These suggested that the suppression effects on microglia activation induced by baicalein administration may be related with regulation of PI3K and NFkB pathway and the potent effects are consistent in different species.

Figure 6:
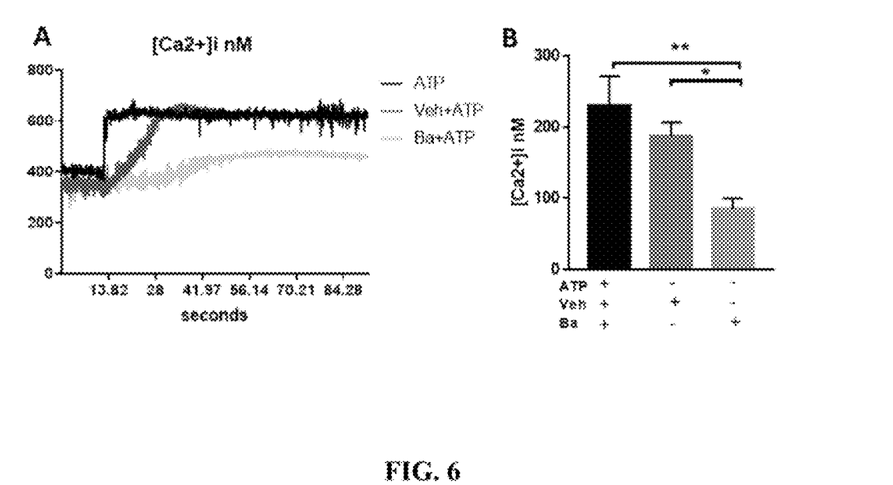
FIG. 6 Pretreat HMC-3 with baicalein for 24 h can inhibit calcium channel activity after ATP stimulation. (A) Changes of $[Ca^{2+}]i$ in cultured HMC-3 with pretreatment of vehicle or 10 µM baicalein for 24 hrs. Elevation of $[Ca^{2+}]i$ was suppressed effectively in baicalein administrated cells. (B) Quantification of $[Ca^2]i$ levels in different treatment groups after stimulation (n=6 cultures/group, and 10-20 neurons were recorded from each group).

Example 2—The elevation of intracellular calcium was inhibited by pretreating HMC-3 with baicalein. Calcium ($Ca^{2+}$) channel activity was found to be involved in the transition of microglia from a surveillance to an active state[18,19]. To verify the effect of baicalein on the influence of microglia state, the measurement of intracellular calcium concentration $[Ca2+]_I$ was applied. After adding 50 µM ATP to microglial cells, the influx of $[Ca2+]_I$ was triggered immediately in naïve group. The elevation of $[Ca2+]_I$ was also shown in vehicle-treated group with longer latency. In contrast, baicalein-treated group showed a delayed $Ca^{2+}$ influx with reduced magnitude (FIGS. 6A and 6B). This demonstrated the capability of baicalein to suppress microglia activation by blocking the elevation of intracellular calcium concentration.

Figure 7:
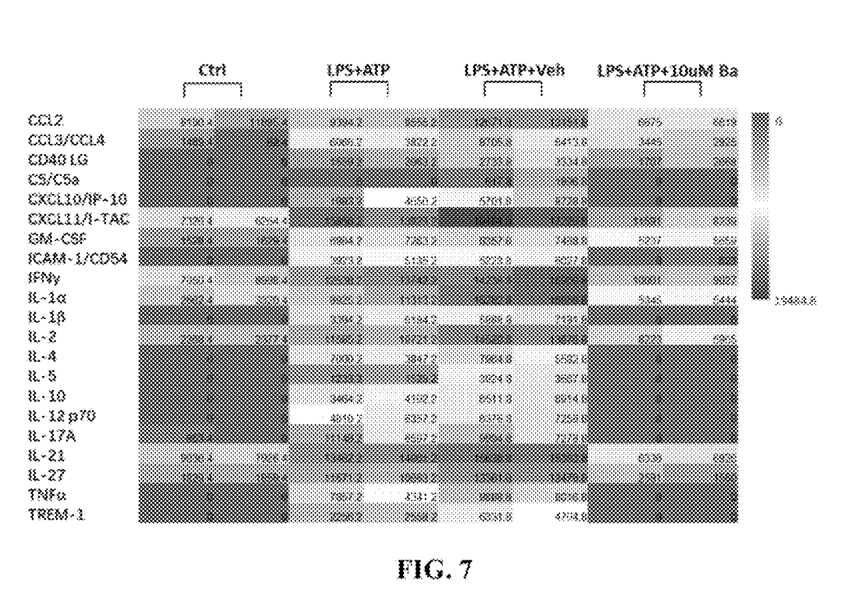
FIG. 7 Baicalein suppresses the expression of pro-inflammatory factors in human microglia HMC3 cell line in vitro. (A) Quantification the averaged pixel density of selected cytokines produced by human microglia cell line HMC-3 culture. (B) The relative expression levels of selected genes (IL-1b, IL-6 and TNFα) were confirmed by qPCR in LPS and ATP control, vehicle, 1 µM or 10 µM baicalein group respectively, naïve control as 1. Error bar=SEM. *P<0.05; **P<0.01. Scale bar=100 µM. One-way ANOVA.

Example 3—Baicalein suppresses the expression of pro-inflammatory factors in human microglia HMC3 cell line in vitro. To further study the role of baicalein on microglia activity, cytokine array and qPCR was utilized to confirm the anti-inflammatory effects. After 6 hours LPS stimulation and additional 30 mins ATP challenge, vehicle, 1 µM or 10 µM baicalein was delivered to the culture media for an additional 42 hours. The culture media from different groups was collected for the cytokine array, while the cells were lysed for qPCR to identify the mRNA level. For the different cytokines level, the heatmap revealed that baicalein given can largely draw the release of pro-inflammatory factors to the resting level, such as CCL2, Cxcl10, IL-1α, IL-10, TNFα, etc (FIG. 7A). At the same time, the mRNA fold changes of IL-1β and TNFα from baicalein delivered cells showed consistent anti-inflammation effects by comparing with the vehicle group (FIG. 7B). The expression of IL-10 and TNFα in baicalein given group were dramatically dropped compared with vehicle group. IL-6 expression level also got significant suppression by baicalein given. All together suggested that baicalein has potent inhibition effects on the immune activities in the retina post-ischemia/reperfusion injury.

REFERENCES

ADDIN EN.REFLIST 1 Minhas, G., Sharma, J. & Khan, N. Cellular Stress Response and Immune Signaling in Retinal Ischemia-Reperfusion Injury. *Frontiers in immunology* 7, 444-444, doi:10.3389/fimmu.2016.00444 (2016).

2 Amakura, Y., Yoshimura, A., Yoshimura, M. & Yoshida, T. Isolation and characterization of phenolic antioxidants from *Plantago* herb. *Molecules* 17, 5459-5466 (2012).

3 Xiao, J.-R., Do, C.-W. & To, C.-H. Potential therapeutic effects of baicalein, baicalin, and wogonin in ocular disorders. *Journal of Ocular Pharmacology and Therapeutics* 30, 605-614 (2014).

4 Cong, Q. et al. Structure and activities of a novel heteroxylan from *Cassia obtusifolia* seeds and its sulfated derivative. *Carbohydrate research* 393, 43-50 (2014).

5 Dinda, B. et al. Therapeutic potentials of baicalin and its aglycone, baicalein against inflammatory disorders. *European journal of medicinal chemistry* 131, 68-80 (2017).

6 Liu, A. et al. Baicalein protects against polymicrobial sepsis-induced liver injury via inhibition of inflammation and apoptosis in mice. 748, 45-53 (2015).

7 Bae, M.-J. et al. Baicalein induces CD4+ Foxp3+ T cells and enhances intestinal barrier function in a mouse model of food allergy. 6, 1-11 (2016).

8 Ma, X. et al. Baicalein suppresses metastasis of breast cancer cells by inhibiting EMT via downregulation of SATB1 and Wnt/β-catenin pathway. 10, 1419 (2016).

9 Huang, Z. et al. Chinese herbal medicine for acute upper respiratory tract infections and reproductive safety: a systematic review. 2018.01298 (2019).

10 Kim, D. H. et al. Gluco-obtusifolin and its aglycon, obtusifolin, attenuate scopolamine-induced memory impairment. *Journal of pharmacological sciences* 111, 110-116 (2009).

11 Gasiorowski, K. et al. Flavones from root of *Scutellaria baicalensis* Georgi: drugs of the future in neurodegeneration? *CNS & Neurological Disorders-Drug Targets (Formerly Current Drug Targets-CNS & Neurological Disorders)* 10, 184-191 (2011).

12 Cui, L. et al. Baicalein is neuroprotective in rat MCAO model: Role of 12/15-lipoxygenase, mitogen-activated protein kinase and cytosolic phospholipase A2. *Pharmacology Biochemistry and Behavior* 96, 469-475, doi: https://doi.org/10.1016/j.pbb.2010.07.007 (2010).

13 Miao, G. et al. Mechanisms underlying attenuation of apoptosis of cortical neurons in the hypoxic brain by flavonoids from the stems and leaves of *Scutellaria baicalensis* Georgi. *Neural regeneration research* 9, 1592 (2014).

14 Sowndhararajan, K., Deepa, P., Kim, M., Park, S. J. & Kim, S. Baicalein as a potent neuroprotective agent: A review. *Biomedicine & Pharmacotherapy* 95, 1021-1032 (2017).

15 Mempel, T. R., Henrickson, S. E. & von Andrian, U. H. T-cell priming by dendritic cells in lymph nodes occurs in three distinct phases. *Nature* 427, 154-159, doi:10.1038/nature02238 (2004).

16 Chen, H. et al. Commensal microflora-induced T cell responses mediate progressive neurodegeneration in glaucoma. 9, 1-13 (2018).

17 Rashid, K., Akhtar-Schaefer, I. & Langmann, T. Microglia in Retinal Degeneration. *Frontiers in immunology* 10, 1975-1975, doi:10.3389/fimmu.2019.01975 (2019).

18 Saddala, M. S. et al. Discovery of novel L-type voltage-gated calcium channel blockers and application for the prevention of inflammation and angiogenesis. *Journal of Neuroinflammation* 17, 132, doi:10.1186/s12974-020-01801-9 (2020).

19 Brawek, B. & Garaschuk, O. Microglial calcium signaling in the adult, aged and diseased brain. *Cell calcium* 53, 159-169, doi:10.1016/j.ceca.2012.12.003 (2013).

What is claimed is:

1. A method of treating an ocular nerve injury in a subject in need thereof, the method comprising intravitreally administering once a week a therapeutically effective amount of a pharmaceutical composition comprising baicalein or a pharmaceutically acceptable salt thereof at a concentration of 10-100 uM to the subject for four weeks, wherein the ocular nerve injury comprises an injured retinal ganglion cell and is the result of an ischemia injury, an ischemia-reperfusion injury, or trauma and treatment results in functional rescue of the injured retinal ganglion cell and optionally one or more of a photoreceptor cell and a bipolar cell.

2. The method of claim 1, wherein administration of the compound at least partially inhibits PI3K and NFkB pathway activation in the subject.

3. The method of claim 1, wherein administration of the compound at least partially inhibits expression of IL-1β and TNFα in the subject.

4. The method of claim 1 wherein the subject is a human.

5. A method of treating an ocular neuron, the method comprising contacting the ocular neuron with baicalein or a pharmaceutically acceptable salt thereof at a concentration of 10-100 uM for four weeks, wherein the ocular nerve comprises an injured retinal ganglion cell and is the result of an ischemia injury, an ischemia-reperfusion injury, or trauma and treatment results in functional rescue of the injured retinal ganglion cell and optionally one or more of a photoreceptor cell and a bipolar cell.

6. The method of claim 5, wherein the ocular neuron is contacted with baicalein or a pharmaceutically acceptable salt thereof at a concentration of 100 μM.

* * * * *